(12) United States Patent
Kaizuka

(10) Patent No.: US 7,241,318 B2
(45) Date of Patent: Jul. 10, 2007

(54) HAIR DYE

(75) Inventor: Kazutoshi Kaizuka, Fukuoka (JP)

(73) Assignee: Create Co., Fukuoka (JP)

( * ) Notice: Subject to any disclaimer, the term of this patent is extended or adjusted under 35 U.S.C. 154(b) by 129 days.

(21) Appl. No.: 10/664,442

(22) Filed: Sep. 19, 2003

(65) Prior Publication Data

US 2004/0111810 A1 Jun. 17, 2004

(51) Int. Cl.
*A61K 7/13* (2006.01)

(52) U.S. Cl. .................. 8/405; 8/406; 8/410; 8/414; 8/415; 8/426; 8/465; 8/632; 8/637.1

(58) Field of Classification Search ............... 8/405, 8/406, 410, 414, 415, 426, 465, 632, 637.1
See application file for complete search history.

(56) References Cited

U.S. PATENT DOCUMENTS 4,857,306 A * 8/1989 Roller .................. 424/63
6,540,791 B1 * 4/2003 Dias .................... 8/111

FOREIGN PATENT DOCUMENTS

JP 2000-128750 5/2000

* cited by examiner

*Primary Examiner*—Eisa Elhilo
(74) *Attorney, Agent, or Firm*—Jeffer, Mangeis, Buller & Marmaro, LLP

(57) ABSTRACT

A hair dye contains the powder of a poly-element mineral to improve the coloring and colorfastness of the hair dye.

5 Claims, No Drawings

HAIR DYE

BACKGROUND OF THE INVENTION

1. Field of the Invention

The present invention relates to a hair dye which contains a poly-element mineral to increase the effectiveness and colorfastness of hair dyes applied on hair.

2. General Background and State of the Art

Conventional uiaioxidating hair dyes contain oxidative dyes such as para-phenylene amine or para-amino phenol and acidic dyes that further include contact dyes such as tar-based colorants, as described for example in Japanese application publication no. JP-2000-128750-A. Many other compositions of hair dyes are known. However, there is a need for improvements to hair dyes that can increase the colorfastness of the dye, prevent fading after multiple washes, and improve the feel of the hair after the dye is applied.

INVENTION SUMMARY

The present invention is directed to a hair dye containing poly-element minerals. The poly-element mineral improves the effectiveness of the hair dye by increasing the coloring capacity of the dye, preventing fading after the hair is washed and dried multiple times, decreasing irritation of the scalp after the dye has been applied and improving the stability of the dye in the hair. The poly-element mineral also enhances the feel of the hair when the dyed hair is brushed.

DETAILED DESCRIPTION OF THE PREFERRED EMBODIMENTS

The hair dye of the present invention comprises a known hair dye composition, as for example the hair dye described in the published application entitled "Hair Dye Composition" described in JP-2000-128750-A, combined with a poly-element mineral powder formed by crushing a poly-element mineral. The hair dye may contain between 0.01% to 20% of the poly-element mineral by weight but preferably between 0.01% to 10%. The poly-element minerals present in the hair dye include silicon-based poly-element minerals which may be found for example as perlite, pitchstone, and tourmaline. In addition to releasing anions, these minerals radiate electromagnetic waves (feeble energy) with a wavelength of 4 to 14 µm. These electromagnetic waves generated by the poly-element minerals excite the electrons in the atomic nuclei surrounding the strands of hair in which the hair dye of the present invention is applied. As a result, water clusters are cut or shortened, decreasing the volume of water and increasing the specific gravity. Furthermore, the free water will attach more readily to the external cell membranes allowing the penetration of water and $Ca^{2+}$ within the cells to activate several functions of the cells.

Applying the hair dye containing poly-element minerals to a person's hair increases his or her blood circulation in the scalp and promotes hair growth. In addition, the poly-element minerals release anions which act on the cuticle and the outer layer of a hair strand, to maintain the hair's luster. Hair with damaged follicles significantly benefits from the presence of poly-element minerals in the hair dye. The hair dye causes superior coloring in the hair because the poly-element minerals increase the penetration of the hair dye into the hair strands and limits the departure of the intercellular binding material known as the cell membrane complex from the cortex region of the hair strands. When heat is applied to the dyed hair, the heat combines with the electromagnetic waves emitted by the poly-element minerals to produce far-infrared radiation, which promotes better coloring of the hair and colorfastness of the dye. When the poly-element mineral is mixed with an oxidative dye, the resulting buffering effect mitigates alkali irritation to the hair and scalp. Adding the poly-element mineral to acidic hair dyes and color treatments accelerates the coloring of the hair by increasing the permeation capacity of the dye molecules into the hair strands.

To produce the powdered mixture, a poly-element mineral, such as perlite, pitchstone or tourmaline, may be milled into a powder the size of about 0.5 to 3 µm, preferably 0.5 to 1 µm, for example by using a ball mill. Even though the hair dye may contain only one poly-element mineral, the hair dye preferably contains two or more powdered poly-element minerals. The powder can be used after it has been milled or, alternatively, the milled powder can be further purified by mixing it with water, then heating or pressurizing the solution. Known techniques of vacuum-freeze drying or spray drying the solution can then be used to isolate the powder which is then mixed with the hair dye.

The following chart shows the contents of perlite:

| | |
|---|---|
| silicon dioxide ($SiO_2$) | 71.94% |
| aluminum oxide ($Al_2O_3$) | 14.94% |
| ferrous oxide ($Fe_2O_3$) | 2.54% |
| Magnesium oxide (MgO) | 0.44% |
| calcium oxide (CaO) | 2.47% |
| alkali oxide ($K_2O + Na_2O$) | 6.87% |
| manganese oxide (MnO) | 0.03% |
| phosphoric anhydride ($P_2O_5$) | 0.14% |
| ignition loss | 3.43% |
| drying loss (at 110° C.) | 0.07% |
| other, titanium | trace |

The contents of pitchstone, another poly-element mineral, are shown in the following table:

| | |
|---|---|
| $SiO_2$ | 75.50% |
| $Al_2O_2$ | 14.00% |
| $Fe_2O_2$ | 0.70% |
| $TiO_2$ | 0.03% |
| CaO | 0.34% |
| MgO | 0.03% |
| $K_2O$ | 4.50% |
| $Na_2O$ | 4.30% |
| Ignition loss | 0.60% |

Although the poly-element mineral can be added to the many known types of hair dyes, the poly-element minerals should preferably be added to oxidative, acidic or color treatment (nitro) dyes for optimal results.

The oxidative dyes used in the present invention contain at least one and preferably two or more of the following compounds or any salt thereof in the range of 0.01% to 5% of the weight of the hair dye: 5-amino ortho cresol, ortho amino phenol, ortho chloro para-phenylene diamine, 2-4 diamino phenol, 2,6-diamino pyridine, 4,4'-diamino diphenyl amine, 1,5-dihydroxy naphthalene, diphenyl amine, toluene-2,5-diamine, toluene-3-4-diamine, para-amino phenol, para-phenylene diamine, para-methyl amino phenol, N-phenyl para-phenylene diamine, meta amino phenyl, meta phenylene diamine, resorcin and 2,4-diamino phenoxy ethanol.

The coloring dyes, which are also known as nitro dyes, used in the present invention contain any combination of the following compounds or any salt thereof in the range of 0.01% to 5% of the weight of the hair dye to produce the desired shade or color: 2-nitro para-phenylene diamine, 4-nitro ortho phenylene diamine, 1-amino-2-methyl-6-nitro benzene, 1-amino-2-nitro-4-methyl amino benzene, 4-(2'-hydroxy ethyl)amino-3-nitro-methyl benzene, 1-bis(β-hydroxy ethyl) amino-3-nitro-4-amino benzene, 1-amino-2-(β-hydroxy ethyl)amino-5-nitro benzen 1-hydroxy-3-nitro-4-(3-hydroxy propyl amino) benzene, N,N'-dimethyl-N-hydroxy ethyl-3-nitro para-phenylene diamine, N-methyl-2-nitro para-phenylene diamine, 3-methyl amino-4-nitro phenoxy ethanol, 2-nitro-5-glyceryl-methyl amine, 1-amino-3-methyl-4-(β-hydroxy ethyl)amino-6-nitro benzene and any basic dyes such as Basic Red 76 (C.I. 12245), Basic Brown 16 (C.I. 12250), Basic Brown 17 (C.I. 12251), Basic Yellow (C.I. 12719), Basic Violet 10 (C.I. 45170) and Basic Blue 99 (C.I. 56059).

The acidic dyes used in the present invention contain at least one and preferably two or more of the following compounds in the range of 0.01% to 5% of the weight of the hair dye: 1-(4-sulfo-1-naphthylazo)-2-naphthol-3,6-disulfonic acid trisodium salt, 9-ortho carboxy phenyl-6-hydroxy-2,4,5,7-tetraiodo-3-iso xantone disodium salt, 1-(4-sulfo-1-naphthylazo)-2- naphthol-6,8-disulfonic acid trisodium salt, 9-(4'-sulfo-2'-sulfonium phenyl)-6-diethyl amino-3-(N,N-dithyl imino)-3-iso xanthyl monosodium salt, 3-carboxyl-5-hydroxy-1-para-sulfonyl-4-para-sulfonyl azo pyrazol trisodium salt, 3-carboxy-5-hydroxy-1-para-sulfonyl-4-para-sulfonyl azo pyrazol disodium salt, 1-para-sulfonyl azo-2-naphthol-6-sulfonic acid disodium salt, 4-{[4-(N-ethyl-meta sulfo benzyl amino)-phenyl]-(2-sulfonium phenyl)-methylene}-[1-(N-ethyl-N-meta sulfo benzyl)-$\Delta^{2,5}$-cyclohexadiene imine] disodium salt, 1-para-sulfo phenyl azo-2-naphthol monosodium salt, 9-ortho carboxy phenyl-hydroxy-3-iso xanthone disodium salt, 1-hydroxy-3,6,8-pyrene trisulfonic acid trisodium salt, 4-{[4-(N-ethyl-benzyl amino)-phenyl]-(5-hydroxy-4-sulfo-2-sulfophenyl)-methylene}-(N-ethyl-Nbenzyl-$\Delta^{2,5}$-cyclohexadiene imine) monosodium salt, 2,4-dinitro-1-naphthol-7-sulfonic acid disodium salt, 1-hydroxy-4-(orthosulfo para-tolueno)-anthraquinone monosodium salt and 8-amino-7-para-nitro phenyl azo-2-phenyl azo-1-naphthol-3,6-sulfonic acid disodium salt.

EXAMPLES

The following examples further illustrate the present invention and preferred embodiments. All parts and percentages are by weight unless otherwise indicated.

In Examples 1-3, a hair dye was prepared by mixing each of the components enumerated and pure water to create an aqueous solution. The inventive product samples 1, 2 and 3 in each Example contained different concentrations of the poly-element mineral, but the weight percentage of the other components remained identical.

To conduct the experiments, approximately two grams of the sample hair dye was applied to a small bunch of yak hair having the same approximate weight. The hair dye was left in the yak hair for fifteen minutes in a temperature condition of forty degrees centigrade. Then, the yak hair was shampooed, rinsed and dried to evaluate the coloring capacity of the hair dye. Afterwards, the sequence of shampooing, rinsing and drying was repeated five times to evaluate how quickly the dye faded. Information for each of the inventive product samples and a comparative product sample without a poly-element mineral was recorded.

Example 1

| | Concentration (%) | | | |
|---|---|---|---|---|
| | Inventive Product 1 | Inventive Product 2 | Inventive Product 3 | Comparative Example 1 |
| Perlite | 0.10 | 3.00 | 6.00 | 0.00 |
| Toluene-2,5-diamine sulfate | 1.10 | 1.10 | 1.10 | 1.10 |
| Resorcin | 0.18 | 0.18 | 0.18 | 0.18 |
| 5-amino ortho cresol | 0.08 | 0.08 | 0.08 | 0.08 |
| Para-amino phenol | 0.45 | 0.45 | 0.45 | 0.45 |
| 25% ammonia water | 8.00 | 8.00 | 8.00 | 8.00 |
| Cetostearyl alcohol | 2.00 | 2.00 | 2.00 | 2.00 |
| Polyoxy ethylene cetyl ethyl | 0.50 | 0.50 | 0.50 | 0.50 |
| Lauryl sulfate | 1.00 | 1.00 | 1.00 | 1.00 |
| Pure water | Remainder | Remainder | Remainder | Remainder |
| Coloration | Good | Good | Good | Normal |
| Fading | Good | Good | Good | Poor |

Example 2

| | Concentration (%) | | | |
|---|---|---|---|---|
| | Inventive Product 1 | Inventive Product 2 | Inventive Product 3 | Comparative Example 1 |
| Perlite | 0.10 | 3.00 | 6.00 | 0.00 |
| 8-amino-7-para-nitro phenyl azo-2-phenyl azo-1-naphthol-3,6-disulfonic acid disodium salt | 0.02 | 0.02 | 0.02 | 0.02 |
| 1-hydroxy-4-(ortho sulfo para-toluene)-anthraquinone monosodium salt | 0.02 | 0.02 | 0.02 | 0.02 |
| 1-para-sulfonyl azo-2-naphthol monosodium salt | 0.20 | 0.20 | 0.20 | 0.20 |
| Ethanol | 25.0 | 25.0 | 25.0 | 25.0 |
| Benzyl alcohol | 10.0 | 10.0 | 10.0 | 10.0 |
| Lactic acid | 3.00 | 3.00 | 3.00 | 3.00 |
| Hydroxy ethyl cellulose | 0.50 | 0.50 | 0.50 | 0.50 |
| Pure water | Remainder | Remainder | Remainder | Remainder |
| Coloration | Good | Good | Good | Normal |
| Fading | Good | Good | Good | Poor |

Example 3

| | Concentration (%) | | | |
|---|---|---|---|---|
| | Inventive Product 1 | Inventive Product 2 | Inventive Product 3 | Comparative Example 1 |
| Perlite | 0.10 | 3.00 | 5.00 | 0.00 |
| Nitro para-phenylene diamine | 0.2 | 0.2 | 0.2 | 0.2 |
| Para-nitro meta phenylene diamine sulfate | 0.2 | 0.2 | 0.2 | 0.2 |
| Cetostearyl alcohol | 2.00 | 2.00 | 2.00 | 2.00 |
| Polyoxy ethylene cetyl ethyl | 0.50 | 0.50 | 0.50 | 0.50 |

-continued

| | Concentration (%) | | | |
|---|---|---|---|---|
| | Inventive Product 1 | Inventive Product 2 | Inventive Product 3 | Comparative Example 1 |
| Cetyl trimethyl ammonium chloride | 1.00 | 1.00 | 1.00 | 1.00 |
| Pure water | Remainder | Remainder | Remainder | Remainder |
| Coloration | Good | Good | Good | Normal |
| Fading | Good | Good | Good | Poor |

In Examples 4-9, the hair dye, according to the enumerated composition of each Example, was mixed in equal parts with a 6% solution of hydrogen peroxide before it was applied to the hair. The 6% hydrogen peroxide solution included the following components: hydrogen peroxide (6.0% by weight), salicylic acid (0.05% by weight), a pH adjuster to bring the pH to 2.8, and pure water (remainder). After the hair dye and the hydrogen peroxide solution was applied, the results were recorded. For each of the Examples 4-9, no irritation of the scalp was observed, the resulting hair color was similar to the expected hair color, and the dyed hair could be combed easily. In addition, the hair coloring was stable over time.

Example 4: Brown Hair Dye

| | |
|---|---|
| Perlite | 0.10 |
| Toluene-2,5-diamine sulfate | 0.10 |
| Resorcin | 0.18 |
| 5-amino ortho cresol | 0.08 |
| Para-amino phenol | 0.45 |
| Meta amino phenol | 0.05 |
| 25% ammonia water | 8.00 |
| Lauryl sulfate | 1.00 |
| Cetostearyl alcohol | 4.00 |
| Pure water | Remainder |

Example 5: Afro-Violet Hair Dye

| | |
|---|---|
| Perlite | 0.10 |
| 5-amino ortho cresol | 0.40 |
| Para-amino phenol | 0.40 |
| 25% ammonia water | 8.00 |
| Lauryl sulfate | 1.00 |
| Cetostearyl alcohol | 4.00 |
| Pure water | Remainder |

Example 6: Auburn Hair Dye

| | |
|---|---|
| Perlite | 6.00 |
| Toluene-2,5-diamine sulfate | 0.02 |
| 5-amino ortho cresol | 0.40 |
| Para-amino phenol | 0.40 |
| 25% ammonia water | 8.00 |
| Lauryl sulfate | 1.00 |
| Cetostearyl alcohol | 4.00 |
| Pure water | Remainder |

Example 7: Yellow Hair Dye

| | |
|---|---|
| Perlite | 0.50 |
| Para-nitro meta phenylene diamine sulfate | 0.20 |
| Para-nitro ortho phenylene diamine sulfate | 0.20 |
| 25% ammonia water | 8.00 |
| Lauryl sulfate | 1.00 |
| Cetostearyl alcohol | 4.00 |
| Pure water | Remainder |

Example 8: Golden Yellow Hair Dye

| | |
|---|---|
| Perlite | 3.00 |
| Nitro para-phenylene diamine | 0.30 |
| Para-nitro meta phenylene diamine sulfate | 0.10 |
| Para-nitro ortho phenylene diamine | 0.10 |
| 25% ammonia water | 8.00 |
| Lauryl sulfate | 1.00 |
| Cetostearyl alcohol | 4.00 |
| Pure water | Remainder |

Example 9: Brown Hair Dye

| | |
|---|---|
| Perlite | 2.00 |
| Toluene-2,5-diamine sulfate | 1.10 |
| Resorcin | 0.18 |
| 5-amino ortho cresol | 0.08 |
| Para-amino phenol | 0.45 |
| Basic Brown 6 | 0.01 |
| 25% ammonia water | 8.00 |
| Lauryl sulfate | 1.00 |
| Cetostearyl alcohol | 4.00 |
| Pure water | Remainder |

The acidic hair dye of Example 10 and the orange color treatment of Example 11 were applied without the 6% hydrogen peroxide solution. After the hair dye was applied, the results were recorded. Just as in Examples 4-9, in Examples 10-11 no irritation of the scalp was observed, the resulting hair color was similar to the expected hair color, and the dyed hair could be combed easily. In addition, the hair coloring was stable over time.

Example 10: Brown Acidic Hair Dye

| | |
|---|---|
| Perlite | 1.00 |
| 8-amino-7-para-nitro phenyl azo-2-phenyl azo-1-naphthol-3,6-disulfonic acid disodium salt | 0.02 |
| 1-hydroxy-4-(ortho sulfo para-toluene)-anthraquinone monosodium salt | 0.02 |
| 1-para-sulfonyl azo-2-naphthol monosodium salt | 0.15 |
| Ethanol | 25.0 |
| Benzyl alcohol | 10.0 |
| Lactic acid | 3.00 |
| Hydroxy ethyl cellulose | 0.50 |
| Pure water | Remainder |

Example 11: Orange Color Treatment

| | |
|---|---|
| Perlite | 0.50 |
| Para-nitro meta phenylene diamine sulfate | 0.20 |
| Para-nitro ortho phenylene diamine | 0.20 |
| Nitro para-phenylene diamine | 0.20 |
| Cetyl trimethyl ammonium chloride | 1.00 |
| Cetostearyl alcohol | 4.00 |
| Pure water | Remainder |

In alternative embodiments, pitchstone replaced perlite in the same concentration in Examples 1-11 above. The results when pitchstone was used were similar to the results when perlite was used.

Thus, a hair dye has been disclosed which includes poly-element minerals emit anions and electromagnetic waves to increase the effectiveness of the hair dye and enhances the feel of the hair. In addition to the oxidative, acidic and nitro dyes described above, the hair dye may also include other materials known to be added in hair dyes so long as these do not impair the effect of the present invention. The other materials include, for example, alcohols, fatty acids, silicone, peptides, amino acids, chelating agents, surface active agents, sugars, pilatory agents and perfumes. While variations of the preferred hair dye compositions been disclosed, it would be apparent to those skilled in the art that many more compositions are possible without departing from the inventive concepts herein.

What is claimed is:

1. A hair dye, comprising:
  a water based hair dye including at least one of an oxidative dye, acidic dye and coloring dye; and
  a powder of about 0.01% to 20.0% of the weight of the hair dye, said powder comprising perlite or pitchstone.

2. The hair dye of claim 1, wherein the hair dye further comprises an oxidative dye of about 0.01% to 5.0% of the weight of the hair dye, the oxidative dye comprising a compound from the group consisting of: 5-amino ortho cresol, ortho amino phenol, ortho chloro para-phenylene diamine, 2-4 diamino phenol, 2,6-diamino pyridine, 4,4'-diamino diphenyl amine, 1,5-dihydroxy naphthalene, diphenyl amine, toluene-2,5-diamine, toluene-3-4-diamine, para-amino phenol, para-phenylene diamine, para-methyl amino phenol, N-phenyl para-phenylene diamine, meta amino phenyl, meta phenylene diamine, resorcin, 2,4-diamino phenoxy ethanol, and salts thereof.

3. The hair dye of claim 1, wherein the hair dye further comprises an acidic dye of about 0.01% to 5.0% by weight of the hair dye, the acidic dye comprising a compound from the group consisting of: 1-(4-sulfo-1-naphthylazo)-2-naphthol-3,6-disulfonic acid trisodium salt, 9-ortho carboxy phenyl-6-hydroxy-2,4,5,7-tetraiodo-3-iso xantone disodium salt, 1-(4-sulfo-1-naphthylazo)-2-naphthol-6,8-disulfonic acid trisodium salt, 9-(4'-sulfo-2'-sulfonium phenyl)-6-diethyl amino-3-(N,N-dithyl imino)-3-iso xanthyl monosodium salt, 3-carboxyl-5-hydroxy-1-para-sulfonyl-4-para-sulfonyl azo pyrazol trisodium salt, 3-carboxy-5-hydroxy-1-para-sulfonyl-4-para-sulfonyl azo pyrazol disodium salt, 1-para-sulfonyl azo-2-naphthol-6-sulfonic acid disodium salt, 4-{[4-(N-ethyl-meta sulfo benzyl amino)-phenyl]-(2-sulfonium phenyl)-methylene}-[1-(N-ethyl-N-meta sulfo benzyl)-D2,5-cyclohexadiene imine] disodium salt, 1-para-sulfo phenyl azo-2-naphthol monosodium salt, 9-ortho carboxy phenyl-hydroxy-3-iso xanthone disodium salt, 1-hydroxy-3,6,8-pyrene trisulfonic acid trisodium salt, 4-{[4-(N-ethyl-benzyl amino)-phenyl]-(5-hydroxy-4-sulfo-2-sulfophenyl)-methylene}-(N-ethyl-Nbenzyl-D2,5-cyclohexadiene imine) monosodium salt, 2,4-dinitro-1-naphthol-7-sulfonic acid disodium salt, 1-hydroxy-4-(ortho sulfo para-tolueno)-anthraquinone monosodium salt and 8-amino-7-para-nitro phenyl azo-2-phenyl azo-1-naphthol-3,6-sulfonic acid disodium salt.

4. The hair dye of claim 1, wherein the hair dye further comprises a coloring dye of about 0.01% to 5.0% by weight of the hair dye, the coloring dye comprising a compound selected from the group consisting of: 2-nitro para-phenylene diamine, 4-nitro ortho phenylene diamine, 1-amino-2-methyl-6-nitro benzene, 1-amino-2-nitro-4-methyl amino benzene, 4-(2'-hydroxy ethyl)amino-3-nitro-methyl benzene, 1-bis(b-hydroxy ethyl) amino-3-nitro-4-amino benzene, 1-amino-2-(b-hydroxy ethyl)amino-5-nitro benzene, 1-hydroxy-3-nitro-4-(3-hydroxy propyl amino) benzene, N,N'-dimethyl-N-hydroxy ethyl-3-nitro para-phenylenediamine, N-methyl-2-nitro para-phenylene diamine, 3-methyl amino-4-nitro phenoxy ethanol, 2-nitro-5-glyceryl-methyl amine, 1-amino-3-methyl-4-(b-hydroxy ethyl )amino-6-nitro benzene and salts thereof.

5. The hair dye of claim 4, wherein the coloring dye further comprises a compound selected from the group consisting of: Basic Red 76 (C.I. 12245), Basic Brown 16 (C.I. 12250), Basic Brown 17 (C.I. 12251), Basic Yellow (C.I. 12719), Basic Violet 10 (C.I. 45170) and Basic Blue 99(C.I. 56059).

* * * * *